(12) United States Patent
Hahn et al.

(10) Patent No.: US 9,101,669 B2
(45) Date of Patent: Aug. 11, 2015

(54) SELF-ASSEMBED CONJUGATE AND USE THEREOF

(75) Inventors: Sei Kwang Hahn, Pohang (KR); Kimoon Kim, Pohang (KR); Hyuntae Jung, Pohang (KR); Jeong-A Yang, Cheongju (KR); Kyeng Min Park, Pohang (KR)

(73) Assignee: POSTECH ACADEMY-INDUSTRY FOUNDATION, Pohang (KR)

( * ) Notice: Subject to any disclaimer, the term of this patent is extended or adjusted under 35 U.S.C. 154(b) by 813 days.

(21) Appl. No.: 13/362,205

(22) Filed: Jan. 31, 2012

(65) Prior Publication Data

US 2013/0195751 A1    Aug. 1, 2013

(51) Int. Cl.

| | | |
|---|---|---|
| A61K 31/74 | (2006.01) | |
| A61K 47/38 | (2006.01) | |
| A61K 47/36 | (2006.01) | |
| A61K 31/337 | (2006.01) | |
| A61K 31/513 | (2006.01) | |
| A61K 31/65 | (2006.01) | |
| A61K 31/704 | (2006.01) | |
| A61K 31/713 | (2006.01) | |
| A61K 33/24 | (2006.01) | |
| A61K 39/39 | (2006.01) | |
| A61K 49/00 | (2006.01) | |
| C08B 37/08 | (2006.01) | |
| C08L 5/08 | (2006.01) | |
| A61K 45/06 | (2006.01) | |
| A61K 47/24 | (2006.01) | |
| A61K 9/06 | (2006.01) | |
| A61K 47/34 | (2006.01) | |
| A61K 31/436 | (2006.01) | |
| A61K 31/138 | (2006.01) | |
| A61K 31/4745 | (2006.01) | |
| A61K 31/555 | (2006.01) | |
| A61K 31/7068 | (2006.01) | |
| A61K 47/48 | (2006.01) | |
| A61K 8/11 | (2006.01) | |
| B82Y 5/00 | (2011.01) | |

(52) U.S. Cl.
CPC . *A61K 47/38* (2013.01); *A61K 9/06* (2013.01); *A61K 31/138* (2013.01); *A61K 31/337* (2013.01); *A61K 31/436* (2013.01); *A61K 31/4745* (2013.01); *A61K 31/513* (2013.01); *A61K 31/555* (2013.01); *A61K 31/65* (2013.01); *A61K 31/704* (2013.01); *A61K 31/7068* (2013.01); *A61K 31/713* (2013.01); *A61K 33/24* (2013.01); *A61K 39/39* (2013.01); *A61K 45/06* (2013.01); *A61K 47/24* (2013.01); *A61K 47/34* (2013.01); *A61K 47/36* (2013.01); *A61K 47/4823* (2013.01); *A61K 47/48784* (2013.01); *A61K 49/0043* (2013.01); *A61K 49/0054* (2013.01); *C08B 37/0072* (2013.01); *C08L 5/08* (2013.01); *A61K 8/11* (2013.01); *B82Y 5/00* (2013.01)

(58) Field of Classification Search
CPC ...................................................... A61K 8/11
See application file for complete search history.

(56) References Cited

U.S. PATENT DOCUMENTS 7,388,099 B2 * 6/2008 Kim et al. ............... 548/305.4

FOREIGN PATENT DOCUMENTS

| KR | 10-0484504 B1 | 3/2003 |
|---|---|---|
| KR | 10-0554156 B1 | 2/2005 |
| KR | 10-2011-0076469 | 7/2011 |

* cited by examiner

*Primary Examiner* — Paul Dickinson
(74) *Attorney, Agent, or Firm* — Lexyoume IP Meister, PLLC

(57) ABSTRACT

Provided are a self-assembled conjugate of a host molecule containing compound and a guest molecule containing compound, a delivery composition of a bioactive material comprising the self-assembled conjugate and a bioactive material to be delivered, and a composition for tissue engineering containing the self-assembled conjugate and a cell.

15 Claims, 13 Drawing Sheets

Fig. 4
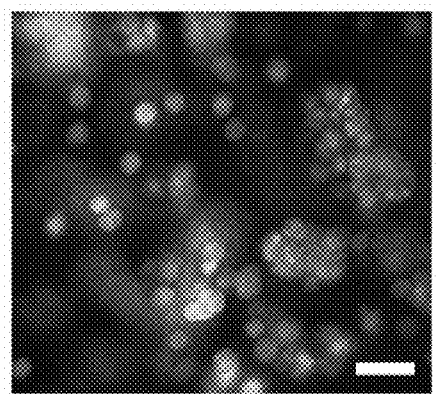
(a)
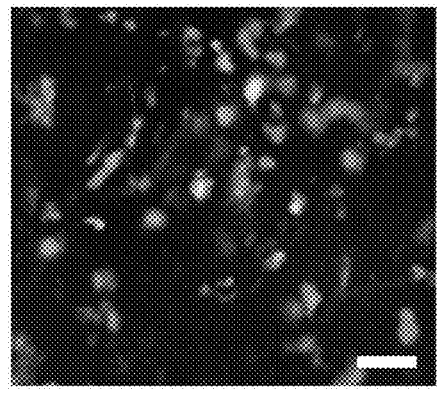
(b)

Fig. 7
(a) 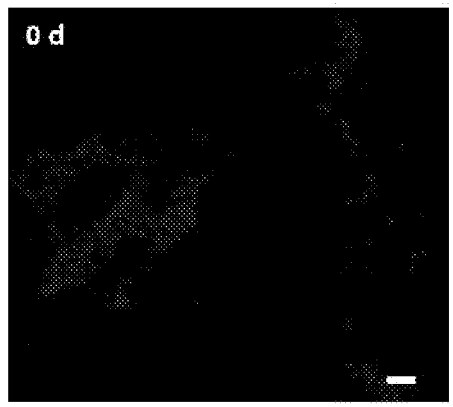 (b) 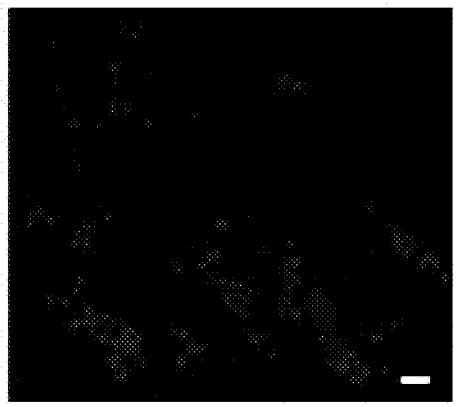
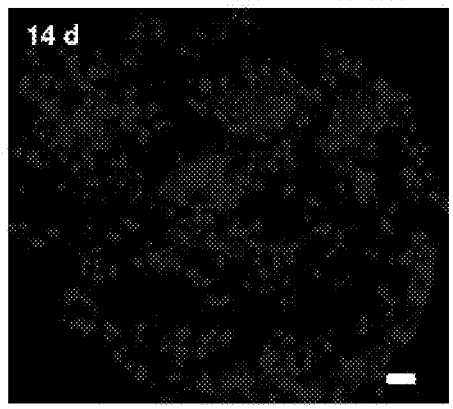 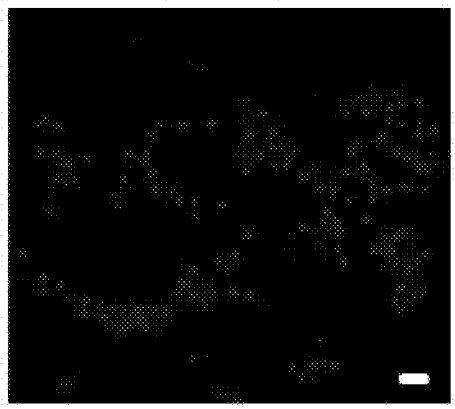
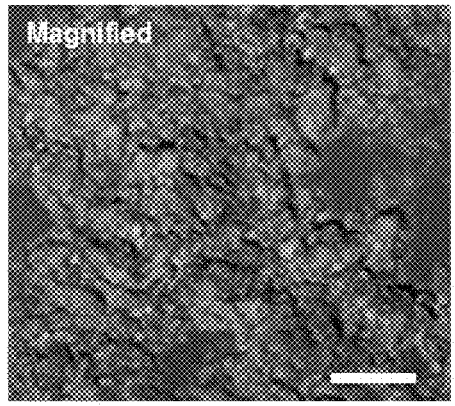 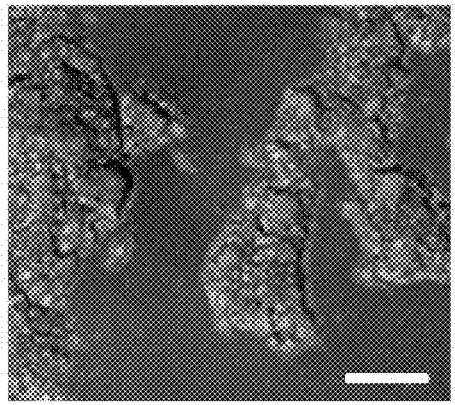

SELF-ASSEMBED CONJUGATE AND USE THEREOF

BACKGROUND OF THE INVENTION (a) Field of the Invention

The present invention relates to a self-assembled conjugate of a host molecule containing compound and a guest molecule containing compound, a delivery composition of a bioactive material comprising the self-assembled conjugate and a bioactive material to be delivered, and a composition for tissue engineering containing the self-assembled conjugate and a cell.

(b) Description of the Related Art

Extracellular matrix (ECM) plays a crucial role in defining the 3D environment of cells. Recently, synthetic hydrogels have emerged as highly promising materials to reconstitute artificial 3D environments that mimic the ECM for both in vitro and in vivo tissue engineering applications. A crucial challenge for such hydrogels is the facile formation and modular modification of the hydrogels in the presence of cells to ensure that cells are exposed to the proper cues for cellular development and differentiation at the right place and time. Strategies for the hydrogel formation and modification generally require highly reactive chemicals, noncovalent interactions such as ionic interactions and hydrogen bonding, and/or external stimuli such as light and temperature or pH change. However, most of these interactions are, up to date, neither controllable nor sufficiently stable in the body, causing a significant cytotoxicity in some cases.

On the other hand, supramolecular hydrogels have been developed using natural host-guest (receptor-ligand) pairs like (strep)avidin-biotin [(S)Av-Bt] with an extremely high binding affinity ($K\sim10^{13}$ to $10^{15}$ $M^{-1}$), but their efficient exploitation has been hampered by the difficulties in chemical modification and mass production as well as the unknown immunogenicity of (S)Av. Alternatively, hydrogels based on synthetic host-guest pairs, such as α-cyclodextrin-polyethyleneglycol (α-CD-PEG) and β-CD-adamantane (β-CD-Ad), have been developed, which have an intrinsic limitation for in vivo applications due to the low binding affinity of CDs to their guests (α-CD-PEG, $K\sim10^2$ $M^{-1}$ and β-CD-Ad, $K\sim10^5$ $M^{-1}$).

Therefore, it has been required to develop materials for the facile formation and modular modification of the hydrogels having low cytotoxicity and low immunogenicity, which are suitable to cell therapy and tissue engineering applications.

SUMMARY OF THE INVENTION

An embodiment provides a self-assembled conjugate of a host molecule containing compound and a guest molecule containing compound, preferably in a hydrogel form.

Another embodiment provides a delivery composition of a bioactive material comprising the self-assembled conjugate and a bioactive material to be delivered.

Still another embodiment provides a composition for tissue engineering containing the self-assembled conjugate and a cell.

DETAILED DESCRIPTION OF THE EMBODIMENTS

In the present invention, a facile in situ supramolecular assembly and modular modification of biomimetic hydrogels are demonstrated using cucurbit[6]uril conjugated hyaluronic acid (CB[6]-HA), diaminohexane conjugated HA (DAH-HA), and tags-CB[6] for tissue engineering applications. The inventors found that a strong and selective host-guest interaction between CB[6] and DAH can make possible the supramolecular assembly of CB[6]/DAH-HA hydrogels in the presence of cells. Then, the 3D environment of CB[6]/DAH-HA hydrogels could be modularly modified by the simple treatment with various multifunctional tags-CB[6]. Furthermore, the inventor could confirm in situ formation of CB[6]/DAH-HA hydrogels under the skin of nude mice by sequential subcutaneous injections of CB[6]-HA and DAH-HA solutions. The inventor could also confirm that the fluorescence of modularly modified fluorescein isothiocyanate (FITC)-CB[6] in the hydrogels was maintained for up to 11 days, reflecting the feasibility to deliver the proper cues for cellular development and differentiation in the body. Taken together, the inventors found that a synthetic host-guest conjugate hydrogels, such as CB[6]/DAH-HA hydrogels, might be successfully exploited as a 3D artificial extracellular matrix for in vitro studies on cellular behaviours, cell therapy, and tissue engineering applications, to complete the present invention.

One embodiment provides a self-assembled conjugate comprising a compound of chemical formula I and a compound of chemical formula II:

[B]$m$-[H]$n$,     (chemical formula I)

[B]$m$-[G]$l$;    (chemical formula II)

in chemical formula I and II,

H, which is a host molecule, is a cucurbit[n]uril (n=5-12) having a functional group selected from the group consisting of an amine group, a carboxyl group, a hydroxyl group, an aldehyde group, an allyloxy group (—O—CH$_2$—CH=CH$_2$), a vinyl group, an acryl group, a thiol group, and a combination thereof;

G, which is a guest molecule, is selected from the group consisting of a C1-C20 aminoalkyl group having at least one amine group and a C1-C20 aminoalkyl group having metallocene;

B, which is a monomer of a polymer compound linked to the host molecule or the guest molecule, is a monomer of a polymer compound having a functional group selected from the group consisting of an amine group, a carboxyl group, a hydroxyl group, an aldehyde group, an allyloxy group (—O—CH$_2$—CH=CH$_2$), a vinyl group, an acryl group, a thiol group, and a combination thereof, wherein the polymer is at least one selected from the group consisting of polyethylene glycol (PEG), poly lactic acid (PLA), poly glycolic acid (PGA), poly lactic-co-glycolic acid (PLGA), hyaluronic acid, chitosan, dextran and cellulose;

m, which is the number of the monomer, is an integer from 1 to 10,000; and n and l, which are the mole number of the host molecule or the guest molecule, respectively, are independently selected from integers from 1 to 10,000, wherein the ratio of m:n or l may be 1:0.2 to 1:1, and the ratio of n:l may be 1:0.1 to 1:10.

The compound of chemical formula I and a compound of chemical formula II may be self-assembled through a host-guest (receptor-ligand) interaction via a non-covalent bond such as a hydrogen bond, a hydrophobic interaction, an electrostatic interaction, a van der Waals interaction, and the like, thereby facilely forming a conjugate. The host molecule, H, is capable of capturing a guest molecule, and the guest molecule, G, is capable of being captured by the host molecule or has a moiety to be captured by the host molecule.

The self-assembled conjugate may be formed in an aqueous solution. Therefore, the self-assembled conjugate containing the compound of chemical formula I and the compound of chemical formula II may be dissolved in an aqueous solvent, such as water, saline, buffer solution, and the like. The appropriate concentration of the compound of chemical formula I and the compound of chemical formula II in the aqueous solution may be properly controlled depending on the purpose to be used, and may be from 0.1 to 10 wt %. In addition, the compound of chemical formula I and the compound of chemical formula II cannot form a self-assembled conjugate under strongly basic condition, such as higher than pH 11, and thus, the aqueous solution may have pH 11 or less.

The self-assembled conjugate may be in a form of hydrogel when the concentration of the compound of chemical formula I and the compound of chemical formula II in the aqueous solution is from 2 to 10 wt %. In addition, as described above, the aqueous solution may have pH 11 or less.

The mixture ratio of equivalent between the compound of chemical formula I and a compound of chemical formula II may be 1:0.1 to 1:10 (equivalent of the compound of chemical formula I:equivalent of the compound of chemical formula II), and preferably 1:0.1 to 1:1 (equivalent of the compound of chemical formula I:equivalent of the compound of chemical formula II or equivalent of the compound of chemical formula II:equivalent of the compound of chemical formula I).

In a preferable embodiment, H is a cucurbit[n]uril (n=6 or 7) linked with a functional group selected from the group consisting of an amine group, a hydroxyl group, an allyloxy group, and a combination thereof; G is selected from the group consisting of spermine (SPM), diaminohexane (DAH), ferrocene methylamine, and a combination thereof; and B is a hyaluronic acid liked with a functional group selected from the group consisting of an amine group, a carboxyl group, a hydroxyl group, an aldehyde group, an allyloxy group, a vinyl group, an acryl group, a thiol group, and a combination thereof.

In particular, a hyaluronic acid (HA), which is used as B, may be a linear polymeric polysaccharide, wherein β-D-N-acetyl glucosamine and β-D-gluconic acid are alternatively linked, and it may be a natural or synthetic hyaluronic acid, or a modified one thereof. The molecular weight of hyaluronic acid may be 0.5 kDa to 1,000 kDa, and specifically 5 kD to 200 kD, but not limited thereto.

The self-assembled conjugate may be useful as a delivery system for controlled release of various therapeutically or biologically useful material (bioactive material) in a living body or a cell separated therefrom, when at least one bioactive material is entrapped thereto. Therefore, a delivery system of a bioactive material may be prepared by mixing the self-assembled conjugate at least one bioactive material to be delivered into a living body or a cell separated therefrom, allowing the bioactive material to be entrapped into the conjugate.

Therefore, another embodiment provides a delivery composition of a bioactive material, comprising the self-assembled conjugate and a bioactive material; and a method of delivering a bioactive material using the self-assembled conjugate. The method of delivering a bioactive material may comprise the step of providing a mixture of the self-assembled conjugate and a bioactive material, wherein the bioactive material is entrapped in the self-assembled conjugate, and administering the mixture of the self-assembled conjugate and a bioactive material to a subject in need of administration of the bioactive material.

The bioactive material may be at least one selected from the group consisting of drugs, fluorescent materials, radioisotopes, target-oriented materials, imaging materials, cells, protein drugs, antibodies, aptamers, and the like.

The subject may be a living body of an animal, and specifically a mammal including a human, or a cell separated therefrom. The route of the administration may be oral or non-oral route, and preferably, the administration may be an injection via subcutaneous, intravenous, intramuscular, or intraperitoneal route.

The drug may be at least one selected from the group consisting of paclitaxel, doxorubicin, docetaxel, 5-fluoreuracil, oxaliplatin, cisplatin, carboplatin, berberine, epirubicin, doxycycline, gemcitabine, rapamycin, tamoxifen, herceptin, avastin, tysabri, erbitux, campath, zevalin, humira, mylotarg, xolair, bexxar, raptiva, remicade, siRNA, aptamer, interferon, insulin, reopro, rituxan, zenapax, simulect, orthoclone, synagis, erythropoietin, epidermal growth factor (EGF), human growth hormone (hGH), thioredoxin, Fel d1, Bee Venom Phospholipase A2 (Api m 1), myelin basic protein, Hsp60, Chaperone DnaJ (Hsp 40), and the like.

The fluorescent material may be at least one selected from the group consisting of fluorescein, rodamine, Dansyl, Cyanine dye (Cy), antracene, and the like.

The radioisotope may be at least one selected from the group consisting of $^3H$, $^{14}C$, $^{22}Na$, $^{35}S$, $^{33}P$, $^{32}P$, $^{125}I$, and the like.

The target-oriented material may be a peptide comprising at least one selected from the group consisting of RGD (arginine-leucine-aspartic acid), TAT (threonine-alanine-threonine), and MVm (methionine-valine-D-methionine); a peptide recognizing a specific cell; an antigen; an antibody; folic acid; nucleic acid; an aptamer; a carbohydrate; and the like.

The imaging material may be a peptide comprising at least one selected from the group consisting of a gadolinium (Ga)-complex selected from gadolinium-diethylenetriamine penta-acetic acid (Ga-DTPA), gadolinium-diethylenetriamine penta-acetic acid-BMA (Ga-DTPA-BMA), gadolinium-tetraazacyclododecanetetraacetic acid (Ga-DOT), and Gadolinium-(1,4,8,11-tetraazacyclotetradecane) (Ga-cyclam); a nanoparticle of a metal selected from gold, silver, manganese, cadmium, selenium, tellurium, zinc, and the like, which has an average diameter of 1 to 200 nm; and a carbon nano-material selected from a single-walled carbon nanotube, a multi-walled carbon nanotube, fullerene, graphene and the like.

The cell may be at least one selected from the group consisting of cancer cells, bone cells, skin cells, stomach cells, intestinal cells, lung cells, liver cells, brain cells, blood endothelial cells, immune cells, eythrocytes, leukocytes, lymphocytes, preosteoblasts, osteoblast, mesenchymal stem cell, induced pluripotent stem cell, and the like, but not be limited thereto.

The protein drug may be at least one selected from the group consisting of Interferon (IFN), human growth hormone (hGH), insulin, Erythropoietin (EPO), Bone morphogenetic protein 2 (BMP-2), TNF-related apoptosis-inducing ligand (TRAIL), granulocyte-colony stimulating factor (G-CSF), and the like, but not be limited thereto.

The preparation of the self-assembled conjugate and the delivery composition of a bioactive material may be conducted referring to Korean patent application no. 10-2009-0133187, the entire contents of which are incorporated herein by reference.

In another aspect, the self-assembled conjugate and/or hydrogel is biocompatible and has a proper intensity for the use in tissue engineering. Therefore, another embodiment provides a composition for tissue engineering containing the self-assembled conjugate and a cell or a method of treatment by using tissue engineering, comprising the step of administering composition for tissue engineering containing the self-assembled conjugate and a cell to a subject in need thereof. The self-assembled conjugate may be in hydrogel form. The cell may be at least one selected from the group consisting of cancer cells, bone cells, skin cells, stomach cells, intestinal cells, lung cells, liver cells, brain cells, blood endothelial cells, immune cells, eythrocytes, leukocytes, lymphocytes, preosteoblasts, osteoblast, mesenchymal stem cell, induced pluripotent stem cell, and the like, but not be limited thereto. Simple mixing of CB[6]-HA with guest modified hyaluronic acid conjugate may produce a hydrogel in situ in the presence of cells without additional reagents and stimuli. For modular modification of the hydrogel, the various tags-CB[6] can be anchored at the residual DAH moieties on the hydrogel by host-guest chemistry for cell proliferation and differentiation.

For achieving an excellent efficacy, the content of the cell in the self-assembled conjugate or hydrogel may be 500,000~2,000,000 cells based on 1 ml of 2 wt % self-assembled conjugate aqueous solution (or hydrogel).

Alternatively, the composition for tissue engineering may contain the self-assembled conjugate and one or more selected from the group consisting of a cell-differentiation inducer, a cell-growth factor, a cell-proliferation accelerator, a cell-adsorption inducer, and the like which can be useful in growth, proliferation, and/or differentiation of cells, with or without the cell. In addition, provided is a method of treatment by using tissue engineering, comprising the step of administering composition for tissue engineering to a subject in need thereof.

The cell-differentiation inducer may be at least one selected from the group consisting of 2-(4-methoxyanilino)-4-(1-hydroxyethylamino)pyrimidine, 3-(3-(2-(3,4,5-tri-methoxy-phenylamino)-7H-pyrrolo[2,3-d]pyrimidin-7-yl) phenyl)propionitrile, chromeceptin, 2-(4-morpholinoanilino)-6-cyclohexylaminopurine, 2-(1-naphthoxy)-6-(4-morpholinoanilino)-9-cyclohexylpurine), and the like, but not be limited thereto.

The cell-growth factor may be at least one selected from the group consisting of vascular endothelial growth factor, epidermal growth factor, hepatocyte growth factor, and the like, but not be limited thereto.

The a cell-proliferation accelerator may be at least one selected from the group consisting of RGD peptide, cyclic RGD peptide, and the like, but not be limited thereto.

The cell-adsorption inducer may be at least one selected from the group consisting of RGD peptide, cyclic RGD peptide, and the like, but not be limited thereto.

In the delivery composition a bioactive material and the composition for tissue engineering, their gel intensity and degradation rate can be properly adjusted by the kind of the guest molecule.

Cucurbit[n]uril (n=5-12, preferably 5-8 and 10, more preferably 6; CB[n]), which is a member of the hollowed-out-pumpkin-shaped host family, has exceptionally high binding affinity and selectivity toward alkyl ammonium ions in aqueous solution. In particular, it tightly binds polyamines (PA) like 1,6-diaminohexane (DAH) or spermine (SPM) (in their protonated forms) to make ultrastable 1 to 1 host-guest complexes with a binding constant up to $10^{10}$ $M^{-1}$ or $10^{12}$ $M^{-1}$, M which is almost comparable to that of streptavidin and biotin (SAv-Bt, K~$10^{13}$ $M^{-1}$). The exceptional selectivity and stability under physiological conditions, as well as negligible cytotoxicity, make CB-PA pairs a useful tool for the noncovalent conjugation and modification of CB-based nanomaterials.

In a representative embodiment, the present inventors report a facile supramolecular strategy for the formation of biomimetic hyaluronic acid (HA) hydrogels in the presence of cells taking advantages of the highly selective and strong host-guest interaction of CB[6]-PA as a driving force for the crosslinking of biopolymer chains. As shown in FIG. 1, the approach involves 1) conjugation of a CB[6] derivative to HA for the synthesis of a host-attached HA (CB[6]-HA) and attachment of PA such as DAH or SPM to HA for the preparation of a guest-attached HA (DAH-HA or SPM-HA), 2) simple mixing of CB[6]-HA with either DAH-HA or SPM-HA to produce a hydrogel in situ in the presence of cells without additional reagents and stimuli, and 3) further modular modification of the hydrogel with various "tags"-attached CB[6] (tags-CB[6]), which can be anchored at the residual DAH moieties on the hydrogel by host-guest chemistry. HA is a naturally occurring linear polysaccharide in the body and one of main components of ECM. The CB[6]/PA-HA hydrogels with a good mechanical stability, enzymatic degradability, and negligible toxicity are assessed in vitro and in vivo, and expected for various biomedical applications such as 3D cell culture, cell therapy, and tissue engineering.

BRIEF DESCRIPTION OF DRAWINGS

FIG. 4 shows NIH3T3 cells in (a) CB[6]/DAH-HA hydrogels and (b) CB[6]/SPM-HA hydrogels stained with calcein AM (live cells, green) and EthD-1 (dead cells, red) after incubation at 5% CO2 and 37° C. for 3 days (scale bar=50 μm).

FIG. 7 shows confocal laser scanning microscopic images of NHDF cells entrapped in CB[6]/DAH-HA hydrogel (a) with or (b) without the treatment of c(RGDyK)-CB[6] after cryosectioning and staining with DAPI. Magnified fluorescence images were taken in 14 days, and overlapped with their respective bright field images (scale bar=50 μm).

EXAMPLE

Figure 1A:
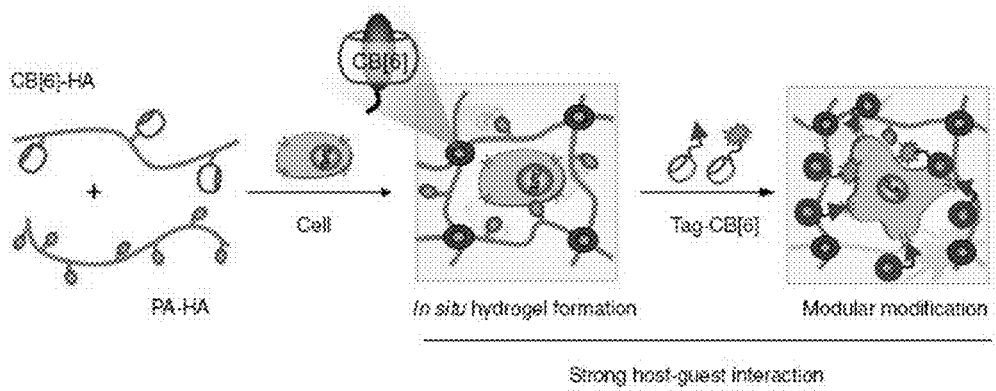
FIG. 1a shows a schematic representations for in situ formation of supramolecular biomimetic hydrogel and its modular modification using highly selective and strong host-guest interactions, wherein CB[6]/PA-HA hydrogel was formed by the simple mixing of CB[6]-HA and PA-HA, and modified with various tags-CB[6].
Figure 1B:
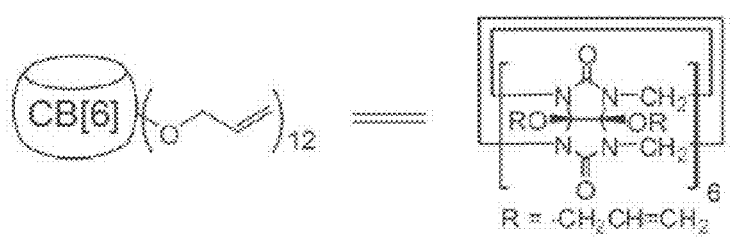
FIG. 1b shows chemical structures of CB[6].
Figure 1C:
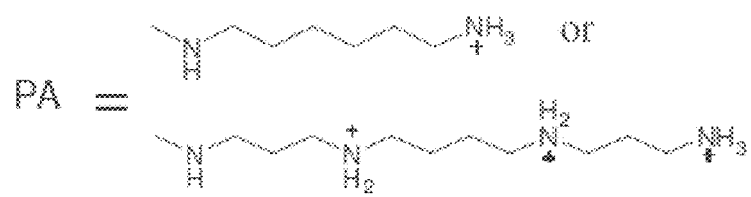
FIG. 1c shows chemical structures of PA (DAH or SPM).

The present invention is further explained in more detail with reference to the following examples. These examples, however, should not be interpreted as limiting the scope of the present invention in any manner.

Materials

Sodium hyaluronate, sodium salt of hyaluronic acid (HA), with a molecular weight (MW) of 100 kDa was obtained from Shiseido (Tokyo, Japan) and HA with a MW of 234 kDa was purchased from Lifecore (Chaska, Minn.). Hyaluronidase from *Streptomyces hyalurolyticus*, phosphate buffered saline (PBS) tablet, 1,6-diaminohexane (DAH), fluorescein isothiocyanate (FITC), and rhodamine B isothiocyanate (RBITC) were purchased from Sigma (St. Louis, Mo.). Spermine (SPM) was obtained from Tokyo Chemical Industry (Tokyo, Japan). The acetomethoxy derivative of calcein (Calcein AM), ethidium homodimer-1 (EthD-1), and 4',6-diamidino-2-phenylindole (DAPI) were obtained from Molecular Probes (Carlsbad, Calif.). Cyclic RGDyK peptide [c(RGDyK)] was purchased from Peptron (Daejeon, Korea). SnakeSkin pleated dialysis tube was obtained from Thermo Scientific (Rockford, Ill.). Mouse embryonic fibroblast (NIH3T3) and normal human dermal fibroblast (NHDF) cell lines were obtained from American Type Culture Collection (ATCC). Dulbecco's modified eagle's medium (DMEM), fetal bovine serum (FBS), and penicillin/streptomycin (PS) were obtained from HyClone (Logan, Utah). Optimal cutting temperature (OCT) compounds (TISSUE-TEKs 4583) were purchased from Sakura Finetek (Torrance, Calif.) and Balb/c nude mice were obtained from Clea in Japan. All reagents were used without further purification. Animal experiments were approved by the Animal Care Committee of CHA University.

Example 1

Preparation and Characterization of CB[6]/PA-HA Hydrogels

CB[6]-conjugated HA (CB[6]-HA) was synthesized by thiol-ene "click" reaction of thiol-functionalized HA (HS-HA, MW=100 kDa) with $(allyloxy)_{12}CB[6]$ as reported previously (Kim, K.; Selvapalam, N.; Ko, Y. H.; Park, K. M.; Kim, D.; Kim, K. Functionalized cucurbiturils and their applications. *J. Chem. Soc. Rev.* 2007, 36, 267-279/Jung, H.; Park, K. M.; Yang, J. A.; Oh, E. J.; Lee, D. W.; Park, K. T. et al. Theranostic Systems Assembled In Situ On Demand by Host-Guest Chemistry. *Biomaterials* 2011, 32, 7687-7694, which are incorporated herein by reference). The photoreactions were performed in a quartz tube by UV light using a RMR-600 (Rayonet, Branford, Conn.) photochemical reactor equipped with four 254 nm lamps and four 300 nm lamps. The resulting CB[6]-HA was analyzed by FT-IR (PerkinElmer, Waltham, Mass.) and $^1$H NMR (DRX500, Bruker, Germany). As a counterpart to CB[6]-HA for the hydrogel formation, two different alkylammonium-conjugated HAs, DAH-HA (MW=270 kDa) and SPM-HA (MW=320 kDa), were synthesized and characterized as reported previously (Oh, E. J.; Park, K.; Kim, K. S.; Kim, J.; Yang, J. A.; Kong, J. H. et al. Target specific and long-acting delivery of protein, peptide, and nucleotide therapeutics using hyaluronic acid derivatives. *J. Control. Release* 2010, 141, 2-12/Jung, H.; Park, K. M.; Yang, J. A.; Oh, E. J.; Lee, D. W.; Park, K. T. et al. Theranostic Systems Assembled In Situ On Demand by Host-Guest Chemistry. *Biomaterials* 2011, 32, 7687-7694, which are incorporated herein by reference).

Example 2

Preparation of CB[6]/DAH-HA Hydrogel or CB[6]/SPM-HA Hydrogel

A solution of DAH-HA or SPM-HA (300 μL, 2.0 wt %) in PBS was added to the equal volume of CB[6]-HA solution (2.0 wt %) in PBS. Vortexing the solution mixture for 10 s produced a hydrogel.

Figure 2A:
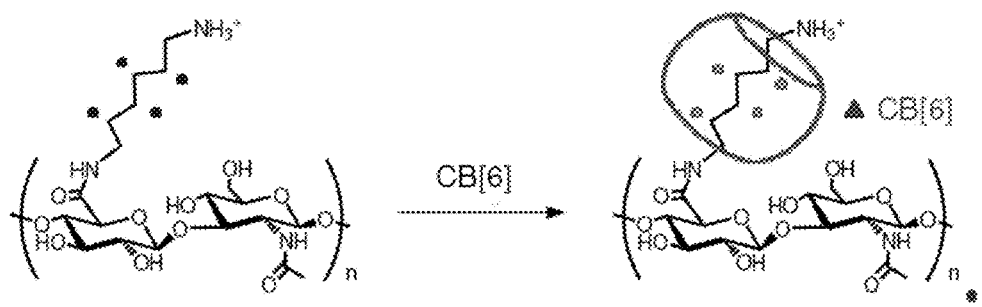
FIG. 2a a schematic representation for the host-guest interaction of DAH-HA with CB[6].
Figure 2B:
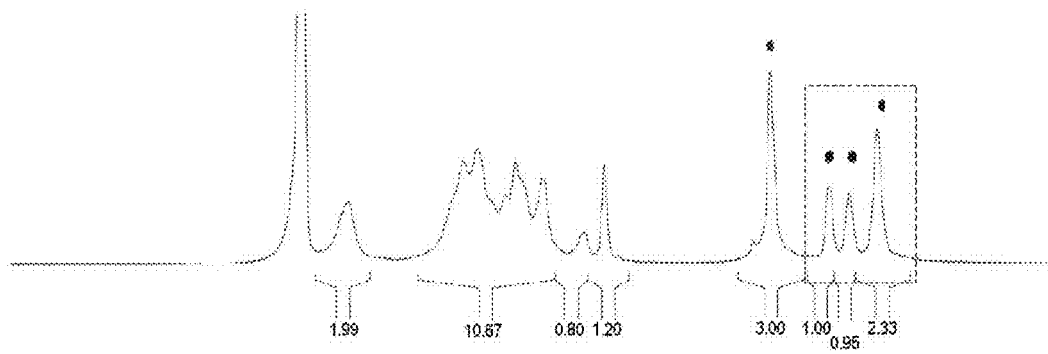
FIG. 2b is a $^1$H NMR spectra of DAH-HA (50±2 mol % DAH on HA units).
Figure 2C:
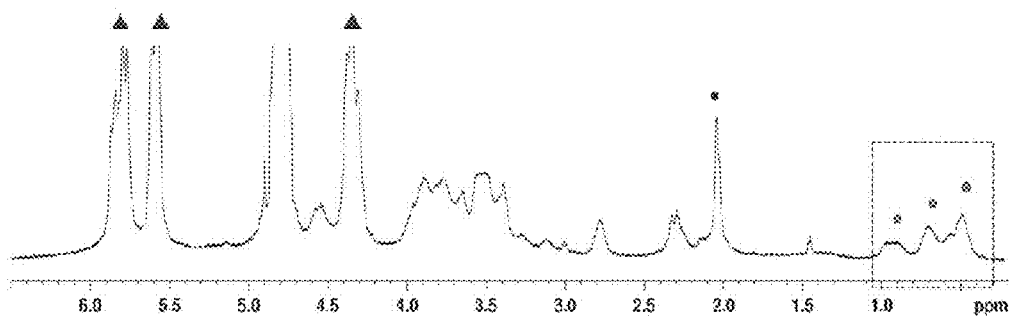
FIG. 2c is a $^1$H NMR spectra of DAH-HA modularly modified with CB[6] by simple mixing in aqueous solution.
Figure 2D:
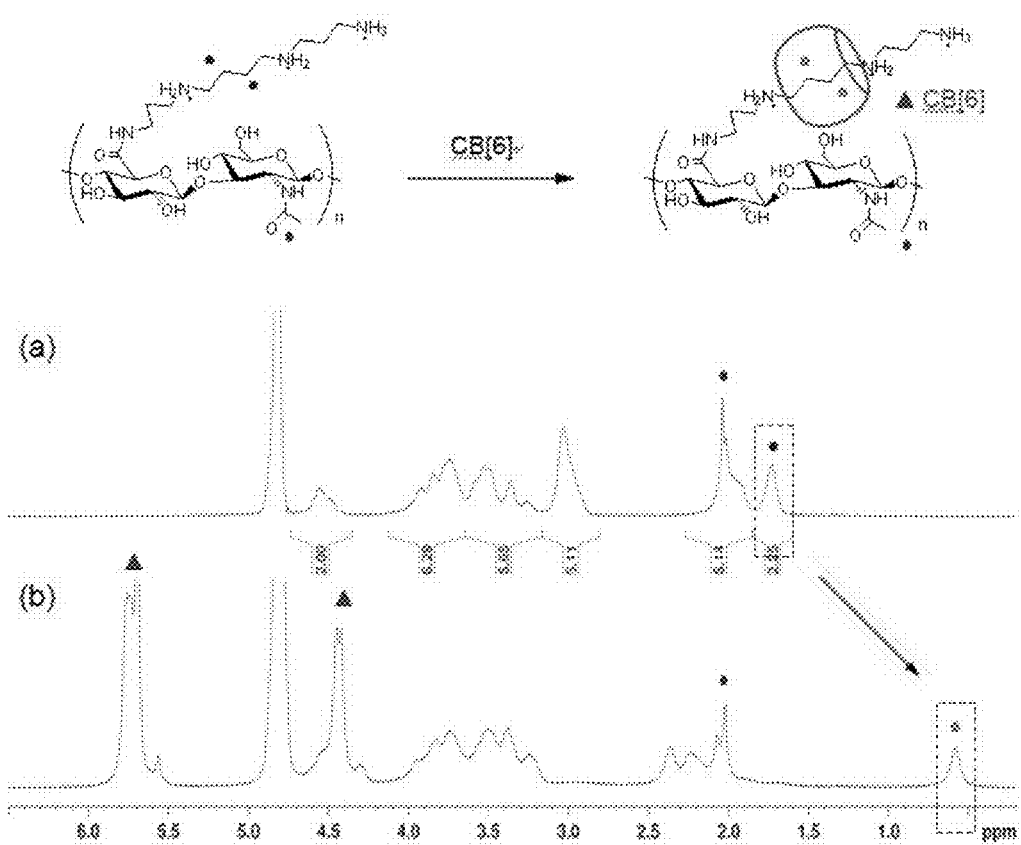
FIG. 2d is $^1$H NMR spectra of SPM-HA (a) before and (b) after addition of CB[6].

CB[6]-HA was synthesized by thiol-ene "click" reaction of HS-HA with $(allyloxy)_{12}CB[6]$ as described above. The successful conjugation of $(allyloxy)_{12}CB[6]$ to HS-HA was confirmed by FT-IR and $^1$H NMR analyses. The integral ratio on the $^1$H NMR spectrum suggested that 6±1 mol % of HA units on average were modified with $(allyloxy)_{12}CB[6]$. DAH-HA and SPM-HA were also synthesized as a counterpart to CB[6]-HA for the hydrogel formation.[24] Approximately 50±2 mol % and 52±2 mol % of HA units on average were modified with DAH and SPM, respectively (FIGS. 2a and S1a in Supporting Information). The ability of DAH or SPM moieties on HA to form host-guest complexes with CB[6] was evidenced by the peak shift from 1.4~1.8 ppm to 0.3~1.0 ppm for DAH or from 1.7 ppm to 0.5 ppm for SPM (FIGS. 2b and S1b) on the $^1$H NMR spectra corresponding to the aliphatic protons of the alkylammonium units included in the cavity of CB[6]. The simple mixing of equal volumes of CB[6]-HA (300 μL, 2.0 wt %) and DAH-HA (300 μL, 2.0 wt %) solutions for 10 s produced a CB[6]/DAH-HA hydrogel (see FIG. 2d). FIG. 2d shows $^1$H NMR spectra of SPM-HA (a) before and (b) after addition of CB[6]. (a) shows that successful conjugation of SPM (52±2 mol % on HA units) on HA (230 kDa) was confirmed by the appearance of the peaks at 3.0 and between 1.6 and 2.1 ppm on $^1$H NMR corresponding to SPM groups. (b) shows that host-guest interaction of DAH-HA with CB[6] was confirmed by the appearance of a characteristic inclusion peak at 0.6 ppm shifted from 1.7 ppm on $^1$H NMR spectrum after treatment with CB[6].

Figure 3:
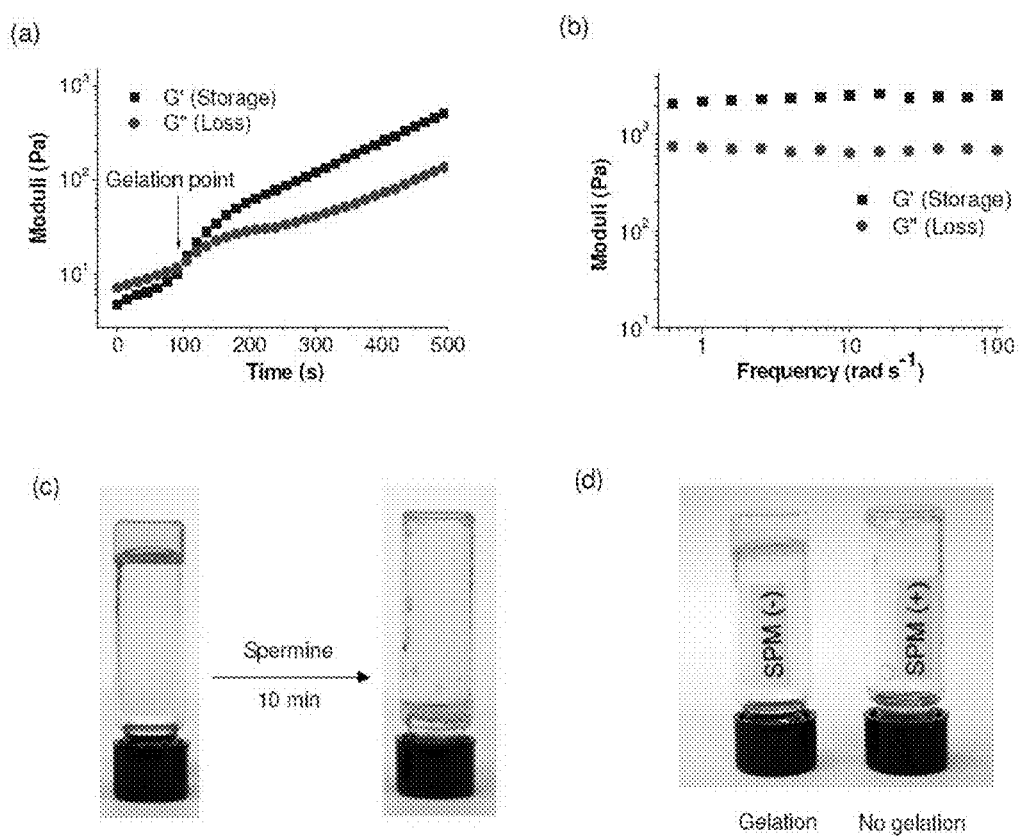
In FIG. 3, (a) shows a time sweep rheological analysis at a constant frequency of 100 rad/s, (b) shows a frequency sweep rheological analysis for storage (G') and loss (G") moduli of CB[6]/DAH-HA hydrogel, (c) shows a phase transition from gel to sol upon addition of excess amount of spermine (SPM) to CB[6]/PA-HA hydrogel, and (d) shows inhibition of the CB[6]/DAH-HA hydrogel formation by the addition of excess amount of SPM (1.0 mg) to CB[6]-HA solution (300 μL, 2.0 wt %) before mixing with DAH-HA solution (300 μL, 2.0 wt %).

The formation of CB[6]/DAH-HA hydrogel was also monitored by dynamic time sweep rheological analysis (FIG. 3(a)).

Rheological analysis was performed on a TA ARES rheometer with a parallel-plate geometry (20 mm diameter) at 25° C. The initial hydrogel formation of the precursor solution (2.0 wt %) was observed by monitoring storage (G') and loss (G") moduli at a constant frequency of 100 rad/s with a fixed strain amplitude (10%) as a function of time. After complete gelation, the storage and loss moduli of a round shape molded CB[6]/DAH-HA hydrogel (1.0 cm in diameter and 0.3 mm in thickness) was monitored at a constant strain amplitude (10%) as a function of frequency to assess the mechanical property of the CB[6]/DAH-HA hydrogel.

The gelation point at which G' (storage modulus) and G" (loss modulus) cross was observed within 2 min at a constant frequency of 100 rad/s. The storage modulus of the CB[6]/DAH-HA hydrogel (1.0 cm in diameter and 0.3 mm in thickness) was measured to be 2.4±0.2 kPa by the frequency sweep rheological analysis (FIG. 3(b)).

Figure 9:
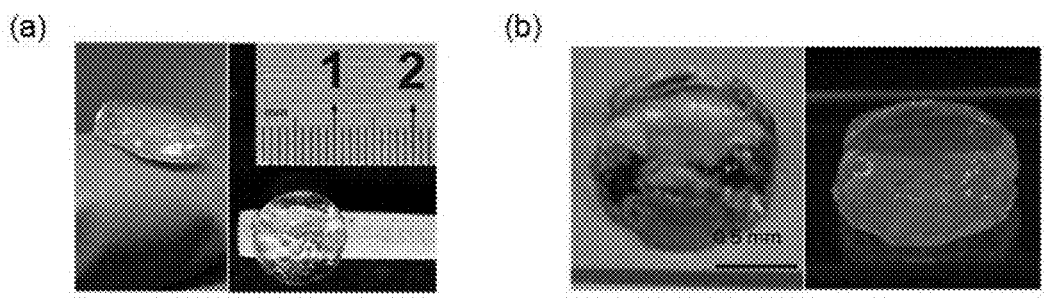
FIG. 9 shows a centimeter scale hydrogel and its modular modification with RBITC-CB[6].

The CB[6]/DAH-HA hydrogel was soft, but robust enough to hold its shape in a centimeter scale (FIG. 9). FIG. 9 shows a centimeter scale hydrogel and its modular modification with RBITC-CB[6]. (a) shows that CB[6]/DAH-HA hydrogel was formed in a cylindrical shape mould by mixing CB[6]-HA (300 μL, 2.0 wt %) and DAH-HA (300 μL, 2.0 wt %) solutions. (b) shows that CB[6]/DAH-HA hydrogel was treated with a solution of RBITC-CB[6] (100 μL, 60 μM) and kept in a humid chamber for 6 h to prepare RBITC-CB[6]@CB[6]/DAH-HA hydrogel. The red color remained even after immersion in PBS for a day.

Figure 10:
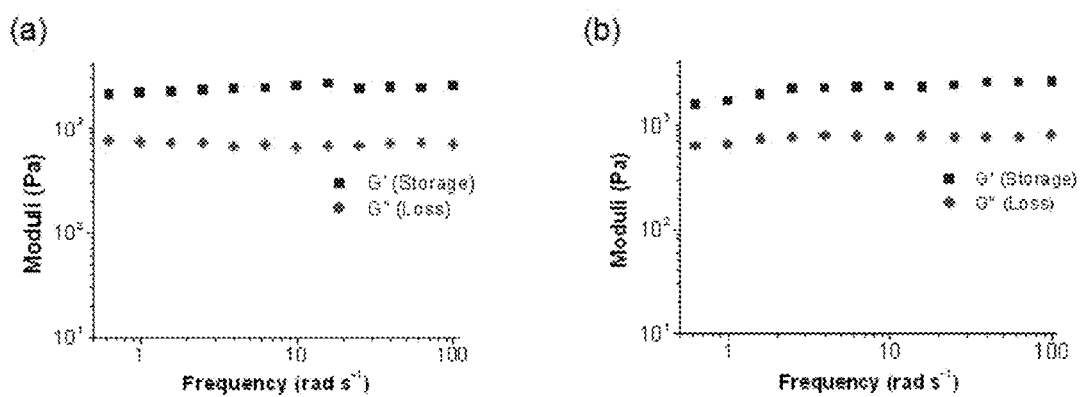
FIG. 10 shows a result of frequency sweep rheological analysis for storage (G') and loss (G") moduli of (a) CB[6]/SPM-HA hydrogel and (b) CB[6]/DAH-HA hydrogel treated with $(HO)_{12}CB[6]$ (0.1 eq. to DAH in CB[6]/DAH-HA hydrogel).

The addition of excess SPM to the hydrogel resulted in a phase transition from gel to sol within 10 min (FIG. 3(c)) and no gelation occurred when CB[6]-HA was added to DAH-HA in the presence of excess SPM (FIG. 3(d)). The results suggested that the host-guest interaction between CB[6] and DAH was responsible for the hydrogel formation. Similar with DAH-HA, SPM-HA also formed a CB[6]/SPM-HA hydrogel upon mixing with CB[6]-HA. Its storage modulus was measured to be 3.4±0.5 kPa, 1.4-fold higher than that of the CB[6]/DAH-HA hydrogel (FIG. 10(a)), which could be ascribed to the stronger host-guest interaction between SPM and CB[6] than that between DAH and CB[6]. From the results, it was thought that a diverse array of hydrogels with different physical and mechanical properties might be prepared by altering the binding affinity of guest molecules. FIG. 10(a) shows a result of frequency sweep rheological analysis for storage (G') and loss (G") moduli of CB[6]/SPM-HA hydrogel treated with $(HO)_{12}CB[6]$ (0.1 eq. to DAH in CB[6]/DAH-HA hydrogel). The average storage modulus (G') of the CB[6]/SPM-HA hydrogel (2.0 wt %) was measured to be 3.4±0.5 kPa which was 1.4 fold higher than that of the CB[6]/DAH-HA hydrogel (2.4±0.2 kPa). Storage modulus (G') of a CB[6]/DAH-HA hydrogel treated with $(HO)_{12}$ CB[6] (0.1 eq. to DAH in CB[6]/DAH-HA hydrogel) was measured to be 2.2±0.3 kPa. The rheology experiment was performed under the same conditions as for the CB[6]/DAH-HA hydrogel (2.0 wt %).

Example 3

Cytocompatibility of CB[6]/DAH-HA Hydrogels

To test in situ formation of CB[6]/DAH-HA hydrogels in the presence of cells, DAH-HA (10.0 μL, 2.0 wt %) and CB[6]-HA (10 μL, 2.0 wt %) solutions were mixed with NIH3T3 cells, which readily resulted in the formation of a cell-entrapped hydrogel. The cytotoxicity of the hydrogel to NIH3T3 cells was assessed using the standard live/dead cell assay with calcein AM and EthD-1 for the staining of live (green) and dead (red) cells, respectively. More than ca. 93% of the cells in CB[6]/DAH-HA hydrogels appeared to be alive emitting green fluorescence even after incubation for 3 days (FIG. 4(a)), whereas the cell viability was lower than ca. 62% for the case of CB[6]/SPM-HA hydrogels (FIG. 4(b)).

Example 4

Cell Viability Assessment

To analyze cellular viability, a live/dead assay was performed with calcein AM and ethidium homodimer-1. The two components were added to PBS at a concentration of 2 μg/mL and 4 μg/mL. The cell entrapped hydrogels were then placed in the solution for 30 min and visualized under a fluorescence microscope. Live cells stain green while dead cells uptake the red dye. In addition, the cell-entrapped CB[6]/DAH-HA hydrogels were treated with and without hyaluronidase, and observed under an optical microscope.

Figure 5:
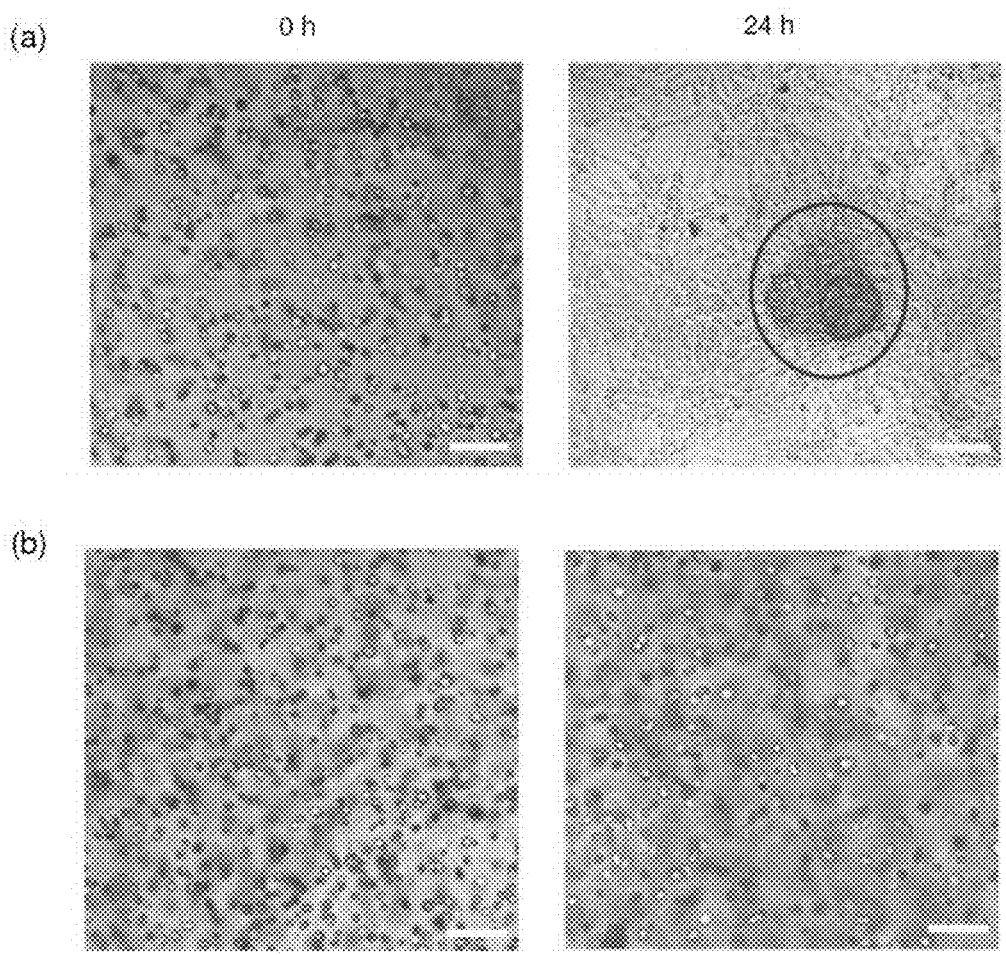
FIG. 5 shows optical microscopic images of cell-entrapped CB[6]/DAH-HA hydrogels after treatment (a) with and (b) without hyaluronidase (scale bar=100 μm), wherein the red circle indicates partial remnants of the CB[6]/DAH-HA hydrogel after enzymatic degradation with hyaluronidase for 24 h.

Since biodegradability is another important property for 3D biomimetic artificial ECM, the enzymatic degradation of the cell-containing CB[6]/DAH-HA hydrogel was examined after treatment with hyaluronidase (HAase), an endoglycosidic enzyme produced by cells to remodel ECM for proliferation and migration in tissues. The hydrogel degraded almost completely in 24 h to release the cells at the bottom of a well plate where they continued to proliferate as observed by optical microscopy (FIG. 5). The in situ formation of hydrogels in the presence of cells with a high cell viability, enzymatic degradability and negligible cytotoxicity is the unique characteristics of CB[6]/DAH-HA hydrogels for the applications to 3D cell culture and tissue engineering.

Example 5

Modular Modification of CB[6]/DAH-HA Hydrogels with "Tags"-CB[6]

Another unique feature of the supramolecular hydrogel is its facile, noncovalent, and modular modification. Within the CB[6]/DAH-HA hydrogels prepared with an equal volume of CB[6]-HA (CB[6] content of 6±1 mol %) and DAH-HA (DAH content of 50±2 mol %) solutions (2 wt % each), a majority of the DAH moieties remain uncomplexed, which can further interact with additional CB[6] derivatives. Accordingly, we could easily modify CB[6]/DAH-HA hydrogels with various functional tags-CB[6] including fluorescent-dye-conjugated CB[6] such as fluorescein isothiocyanate (FITC)-CB[6] and rhodamine B isothiocyanate (RBITC)-CB[6] (FIG. 11) during and even after the hydrogel formation. CB[6]/DAH-HA hydrogels treated with a solution of RBITC-CB[6] (up to 0.1 eq. to DAH moiety on DAH-HA) maintained fluorescence after washing for a day (FIGS. 6(a) and 9(b)).

Figure 11:
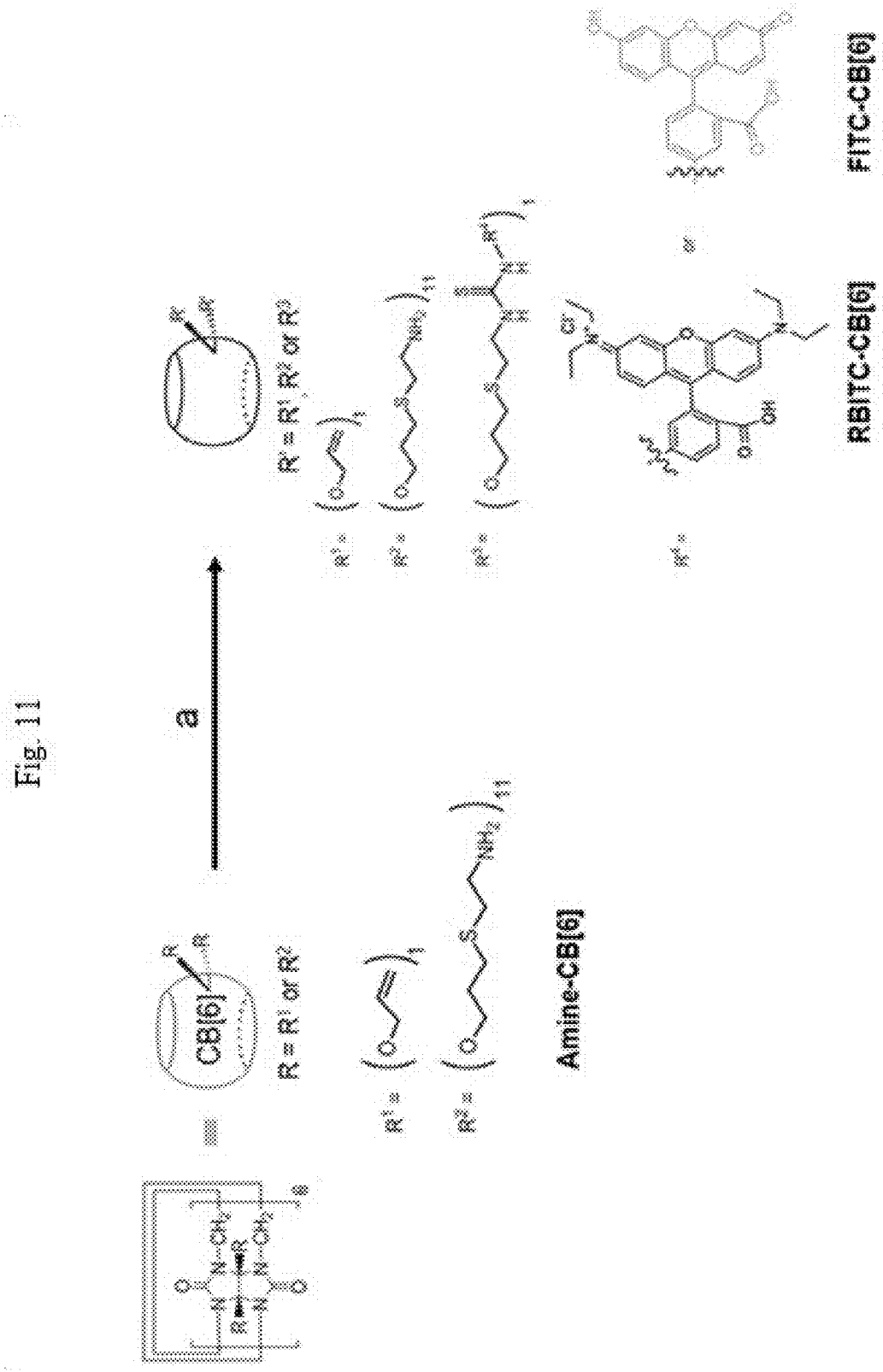
FIG. 11 schematically shows the synthesis of RBITC-CB[6] and FITC-CB[6].

FIG. 11 schematically shows the synthesis of RBITC-CB [6] and FITC-CB[6]. (a) shows that RBITC (6.0 mg, 2.0 eq.)

or FITC (4.0 mg, 2.0 eq.) was added to a solution of amine-CB[6] (20.0 mg) in 50 vol % DMF in distilled water (3.0 mL) and then triethylamine was added until the solution became clear. After stirring at room temperature for a day, the reaction mixture was extensively washed with acetonitrile. The purified product was dried under a reduced pressure to give RBITC-CB[6] (10.0 mg, 40%) or FITC-CB[6] (9.0 mg 37%). $^1$H NMR data suggested that the average substitution number of RBITC or FITC moiety to amine-CB[6] was one. The MALDI-TOF mass spectra revealed species with 1 RBITC or FITC conjugated amine-CB[6] which had 8-12 cysteamines (2-aminoehanethiol) at the periphery of CB[6].

RBITC-CB[6]; $^1$H NMR (500 MHz, $D_2O$): δ 8.73-7.80 (br, 3H), 7.78-6.61 (br, 6H), 5.68 (br, 12H), 4.45 (br, 12H), 4.27-3.43 (br, 32H), 3.26 (br, 24H), 2.90 (br, 12H), 2.79 (br, 12H), 2.09 (br, 24H), 1.51-1.03 (br, 12H). MS (MALDI-TOF): m/z $[M+H]^+$ calcd for $C_{125}H_{200}N_{39}O_{27}S_{13}$ (m=$C_2H_7N_1S_1$, 2-aminoethanethiol), 3095.2. found 3095.6, $[M-m+H]^+$ calcd for $C_{123}H_{193}N_{38}O_{27}S_{12}$, 3018.2. found 3018.5, $[M-2m+H]^+$ calcd for $C_{121}H_{186}N_{37}O_{27}S_{11}$, 2941.1. found 2941.5, $[M-3m+H]^+$ calcd for $C_{119}H_{179}N_{36}O_{27}S_{10}$, 2864.1. found 2864.5, $[M-3m+H]^+$ calcd for $C_{117}H_{172}N_{35}O_{27}S_9$, 2787.1. found 2787.5, $[M-4m+H]^+$ calcd for $C_{115}H_{165}N_{34}O_{27}S_8$, 2710.1. found 2710.4.

FITC-CB[6]; $^1$H NMR (500 MHz, $D_2O$): δ 8.47-7.52 (br, 2H), 7.50-6.50 (br, 5H), 5.68 (br, 12H), 4.45 (br, 12H), 3.77 (br, 24H), 3.26 (br, 24H), 2.90 (br, 12H), 2.79 (br, 12H), 2.09 (br, 24H); MS (MALDI-TOF): m/z $[M+H]^+$ calcd for $C_{117}H_{180}N_{37}O_{29}S_{13}$ (m=$C_2H_7N_1S_1$), 2983.0. found 2983.1, $[M-m+H]^+$ calcd for $C_{115}H_{173}N_{36}O_{29}S_{12}$, 2906.0. found 2906.2, $[M-2m+H]^+$ calcd for $C_{113}H_{166}N_{35}O_{29}S_{11}$, 2829.0. found 2829.2, $[M-3m+H]^+$ calcd for $C_{11}H_{159}N_{34}O_{29}S_{10}$, 2751.9. found 2752.0, $[M-4m+H]^+$ calcd for $C_{109}H_{152}N_{33}O_{29}S_9$, 2674.9. found 2675.1.

Example 6

Modification of CB[6]/DAH-HA Hydrogel with RBITC-CB[6] and/or FITC-CB[6]

A solution of RBITC-CB[6] (50 μL, 60 μM) or RBITC-CB[6] (25 μL, 60 μM)+FITC-CB[6] (25 μL, 60 μM) was added to a CB[6]/DAH-HA hydrogel (600 μL, 2.0 wt %), which was kept in a humid chamber at room temperature for 2 h. The color of the whole hydrogel changed to the color of the RBITC-CB[6] solution. The hydrogel was then immersed in PBS (20 mL) and the PBS was exchanged every 8 h for a day to remove any unbound RBITC-CB[6]. A part of hydrogel, a few hundred micrometers in diameter, was extracted to confirm the successful modification of CB[6]/DAH-HA hydrogel with RBITC-CB[6] or RBITC-CB[6]+FITC-CB[6] under a fluorescence microscope with I3 filters (excitation 450-490 nm and emission>515 nm) for FITC and N2.1 filter (excitation 515-560 nm and emission>580 nm) for RBITC. As a control, the same experiment was performed with RhoB, the unconjugated fluorophore of RBITC instead of RBITC-CB[6]. The relative fluorescence intensity (%) (mean±s.d., n=3) of RBITC-CB[6]@CB[6]/DAH-HA hydrogel and RhoB@CB[6]/DAH-HA hydrogel was monitored for 420 h.

Figure 6:
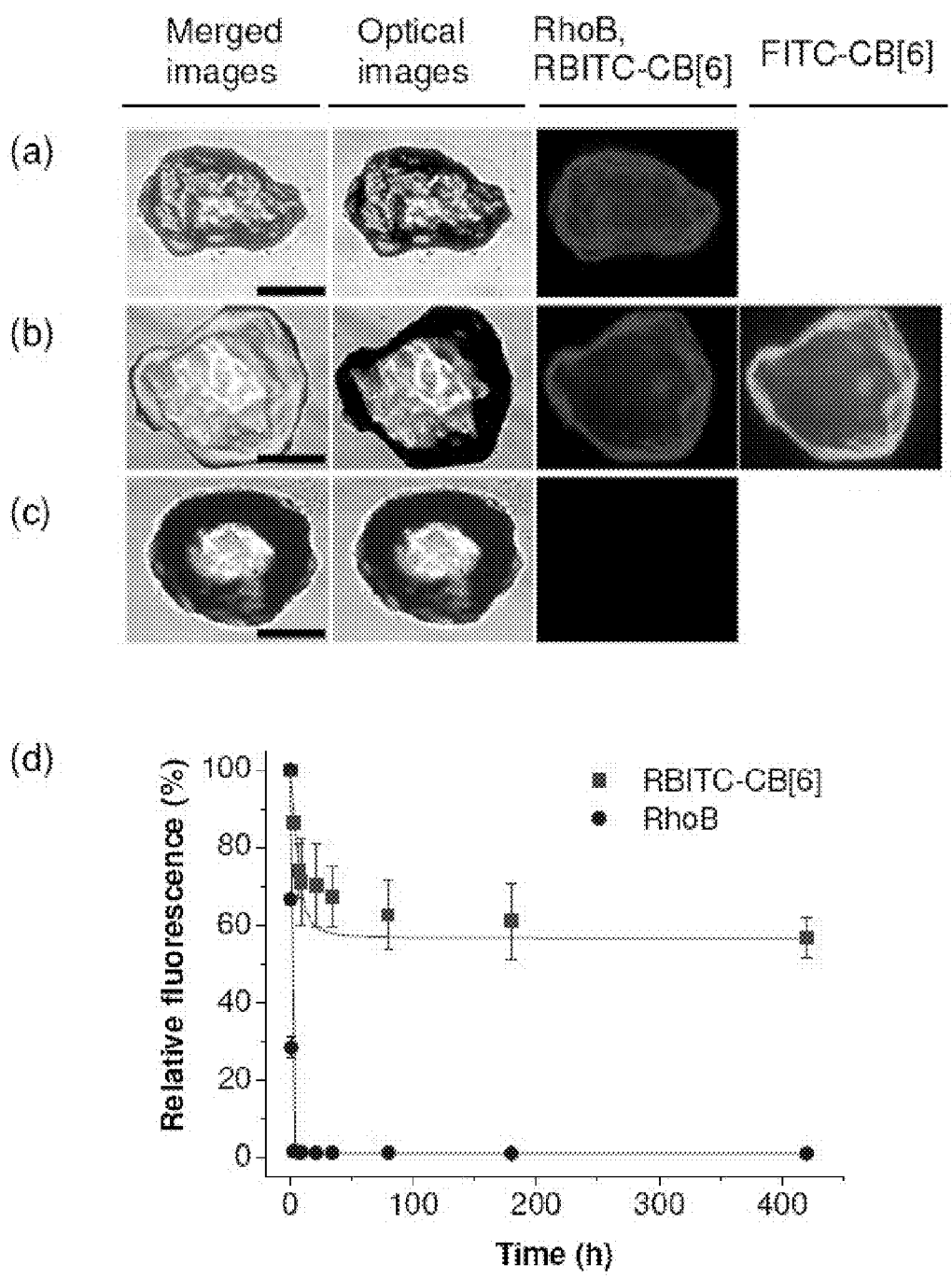
FIG. 6 shows a modular modification of CB[6]/DAH-HA hydrogel with tag-CB[6] by highly selective host-guest interaction, wherein CB[6]/DAH-HA hydrogels treated with (a) RBITC-CB[6], (b) RBITC-CB[6]+FITC-CB[6], and (c) RhoB (Scale bar=100 μm), and (d) shows the relative fluorescence intensity (%) (mean±s.d., n=3) of RBITC-CB[6]@CB[6]/DAH-HA hydrogel and RhoB@CB[6]/DAH-HA hydrogel in PBS with increasing time.

Furthermore, the RBITC-CB[6]@CB[6]/DAH-HA hydrogel retained ca. 60% of the initial fluorescence intensity for up to 3 weeks in PBS (FIG. 6(d)), reflecting the stability of host-guest interaction between the tag-CB[6] and the DAH moiety on the hydrogel. In contrast, CB[6]/DAH-HA hydrogel treated with simple RhoB (the unconjugated fluorophore of RBITC) instead of RBITC-CB[6] showed a rapid decrease in fluorescence intensity (less than 5% of the initial intensity) within 3 h (FIGS. 6(c) and (d)). Interestingly, green and red fluorescence signals were simultaneously observed from CB[6]/DAH-HA hydrogel treated with both FITC-CB[6] and RBITC-CB[6] [(FITC-CB[6]+RBITC-CB[6])@CB[6]/DAH-HA hydrogel] (FIG. 6(b)), demonstrating that several functional groups could be easily introduced at the same time to the supramolecular hydrogel in a modular manner using several different tags-CB[6]. The physical stability of CB[6]/DAH-HA hydrogel was not significantly affected by the treatment with tag-CB[6]. The G' value of the $(HO)_{12}CB[6]@CB[6]/DAH-HA$ hydrogel prepared by mixing CB[6]/DAH-HA hydrogel with 0.1 eq. of $(HO)_{12}CB[6]$ to the DAH moiety in the hydrogel was measured to be 2.2±0.3 kPa (FIG. 10(b)), which was comparable to that of the CB[6]/DAH-HA hydrogel (2.4±0.2 kPa) (FIG. 2b). FIG. 10(b) shows the result of frequency sweep rheological analysis for storage (G') and loss (G") moduli of CB[6]/DAH-HA hydrogel treated with $(HO)_{12}CB[6]$ (0.1 eq. to DAH in CB[6]/DAH-HA hydrogel). The average storage modulus (G') of the CB[6]/SPM-HA hydrogel (2.0 wt %) was measured to be 3.4±0.5 kPa which was 1.4 fold higher than that of the CB[6]/DAH-HA hydrogel (2.4±0.2 kPa). Storage modulus (G') of a CB[6]/DAH-HA hydrogel treated with $(HO)_{12}CB[6]$ (0.1 eq. to DAH in CB[6]/DAH-HA hydrogel) was measured to be 2.2±0.3 kPa. The rheology experiment was performed under the same conditions as for the CB[6]/DAH-HA hydrogel (2.0 wt %).

Example 7

Proliferation of Cells in c(RGDyK)-CB[6]@CB[6]/DAH-HA Hydrogels

To demonstrate the potential of CB[6]/DAH-HA hydrogels as a biomimetic artificial ECM for 3D cell culture, it was conducted to modify the 3D environment of CB[6]/DAH-HA hydrogel with a peptide of c(RGDyK) and investigate the behaviours of cells entrapped in the hydrogels, as follows. The c(RGDyK) is a fibronectin motif known to promote cell adhesion.

7.1. Entrapment of Cells in c(RGDyK)-CB[6]@CB[6]/DAH-HA Hydrogel

NIH3T3(ATCC) and NDHF(ATCC) cells were incubated in high-glucose DMEM containing 10% FBS and 1% PS at 37° C. and 5% $CO_2$. The cells were detached from culture substrates using trypsin, centrifuged with a centrifuge 5810R (Eppendorf) at 700 rpm for 5 mM, and suspended in the solution of CB[6]-HA (2.0 wt %, 1×10$^7$ cells/mL). Each solution of DAH-HA (10.0 μL, 2.0 wt %) and c(RGDyK)-CB[6] (2.0 μL, 11.0 mM) was directly added to the solution of CB[6]-HA (10.0 μL, 2.0 wt %) containing NIH3T3 cells. Then, the solution was mixed to form a cell-entrapped hydrogel. The hydrogel was incubated in 2.0 mL of the culture medium at 5% $CO_2$ and 37° C.

7.2. Cryosectioning of Cell Entrapped Hydrogels

NHDF cells (1×10$^6$ cells) were entrapped in c(RGDyK)-CB[6]@CB[6]/DAH-HA hydrogel (200 μL, 3 wt %) and CB[6]/DAH-HA hydrogel (200 μL, 3 wt %), and incubated at 37° C. and 5% $CO_2$ in DMEM. The hydrogels entrapping cells were taken at 0 day and 14 days, and embedded in OCT compounds to be frozen. The frozen samples were cryosectioned at a thickness of 8 μm and mounted on slide glasses. The sectioned samples were placed in paraformaldehyde (4%) solution containing DAPI (10 μg/mL) for 30 mM and mounted in fluorescent mounting medium. The fluorescence from DAPI was observed with a confocal microscope (Nikon Eclipse TE 2000, Tokyo, Japan) at an excitation wavelength of 405 nm.

Figure 12:
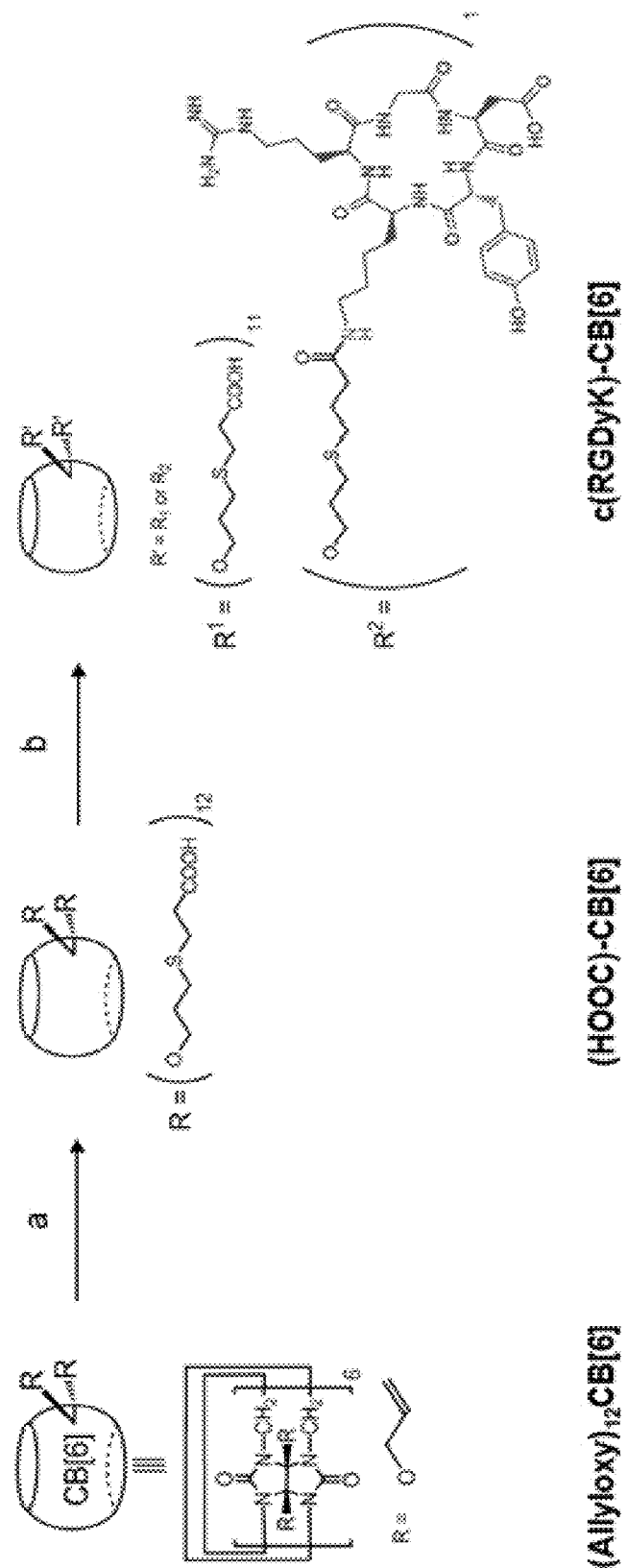
FIG. 12 shows schematics for the synthesis of c(RGDyK)-CB[6].

As described above, a simple treatment of CB[6]/DAH-HA hydrogel with c(RGDyK)-CB[6], synthesized in two steps from (allyloxy)$_{12}$CB[6] (FIG. 12), produced a c(RGDyK)-CB[6]@CB[6]/DAH-HA hydrogel. FIG. 12 shows schematics for the synthesis of c(RGDyK)-CB[6]. In FIG. 12, (a) shows that synthesis of (HOOC)-CB[6]: 3-Mercaptopropionic acid (48 eq., 218.9 mg) was added to a solution of (allyloxy)$_{12}$CB[6] (50.0 mg) in methanol (5.0 mL) and then UV (254 nm and 300 nm) was irradiated to the mixture for 2 days. After evaporation of methanol, the reaction mixture was purified by washing with an excess amount of diethyl ether. The purified product was dried under a reduced pressure to give (HOOC)-CB[6] (110.5 mg, 81.8%). The N/S ratio in elemental analysis suggested that the average substitution number of (HOOC) moiety to (allyloxy)$_{12}$CB[6] was 11.7 which was consistent with the $^1$H NMR data. The MALDI-TOF mass spectrum revealed species with 8~12 3-mercaptopropionic acids conjugated (allyloxy)$_{12}$CB[6]. $^1$H NMR (500 MHz, D$_2$O): δ 5.68 (br, 12H), 4.45 (br, 12H), 3.77 (br, 24H), 2.79 (br, 24H), 2.49 (br, 12H), 2.09 (br, 12H); MS (MALDI-TOF): m/z [M+K]$^+$ calcd for C$_{108}$H$_{156}$N$_{24}$O$_{48}$S$_{12}$K, 2979.7. found 2980.0, [M−m+K]$^+$ (m=C$_{21}$H$_{12}$NO$_5$S, 3-mercaptopropionic acid) calcd for C$_{105}$H$_{150}$N$_{24}$O$_{46}$S$_{11}$K, 2873.7. found 2873.9, [M−2m+K]$^+$ calcd for C$_{102}$H$_{144}$N$_{24}$O$_{44}$S$_{10}$K, 2767.7. found 2767.9, [M−3m+K]$^+$ calcd for C$_{99}$H$_{138}$N$_{24}$O$_{42}$S$_9$K, 2661.7. found 2662.0, [M−4m+K]$^+$ calcd for C$_{96}$H$_{132}$N$_{24}$O$_{40}$S$_8$K, 2555.6. found 2555.8. Analysis (Calcd, found for (C$_{72}$H$_{84}$N$_{24}$O$_{24}$)(C$_3$H$_6$S$_1$O$_2$)$_{11.7}$(H$_2$O$_2$)$_5$) C (42.86, 42.82), H (5.51, 5.54), N (11.20, 11.17), S (12.50, 12.48).

In FIG. 12, (b) shows that Synthesis of c(RGDyK)-CB[6]: c(RGDyK) (1.5 eq. 2.2 mg) was added to a solution of (HOOC)-CB[6] (6.0 mg), N,N'-dicyclohexylcarbodiimide (DCC, 0.8 mg), N-hydroxysuccinimide (NHS, 0.5 mg) and triethylamine (5.0 μL) in DMSO (2.0 mL), which stirred at room temperature for 2 days. After the reaction mixture was purified by dialysis against water using a membrane with a molecular weight cutoff of 1,000, the sample was lyophilized to give c(RGDyK)-CB[6] (6.0 mg, 82%). $^1$H NMR data suggested that the average substitution number of c(RGDyK) moiety to (HOOC)-CB[6] was one. The MALDI-TOF mass spectrum revealed species with 1 c(RGDyK) conjugated (HOOC)-CB[6] which had 8~12 3-mercaptopropionic acids at the periphery of CB[6]. $^1$H NMR (500 MHz, D$_2$O): δ 6.93 (br, 2H), 6.56 (br, 2H), 5.68 (br, 12H), 4.42 (br, 12H), 3.78 (br, 24H), 3.19 (br, 6H), 2.91 (br, 4H), 2.77 (br, 24H), 2.53 (br, 4H), 2.46 (br, 12H), 2.35 (br, 2H), 2.05 (br, 12H), 1.60 (br, 4H), 1.45 (br, 2H); MS (MALDI-TOF): m/z [M+K]$^+$ calcd for C$_{135}$H$_{197}$KN$_{33}$O$_{55}$S$_{12}$ 3581.0. found 3581.5, [M−m+K]$^+$ (m=C$_3$H$_6$O$_2$S) C$_{132}$H$_{191}$N$_{33}$O$_{53}$S$_{11}$K, 3477.0. found 3477.6, [M−2m+K]$^+$ calcd for C$_{129}$H$_{185}$N$_{33}$O$_{51}$S$_{10}$K, 3371.0. found 3371.5, [M−3m+K]$^+$ calcd for C$_{126}$H$_{179}$N$_{33}$O$_{49}$S$_9$K, 3265.0. found 3265.5, [M−4m+K]$^+$ calcd for C$_{123}$H$_{173}$N$_{33}$O$_{47}$S$_8$K, 3159.0. found 3159.5.

Human fibroblast NHDF cells entrapped in the c(RGDyK)-CB[6]@CB[6]/DAH-HA hydrogel proliferated approximately 5-fold in 14 days (FIG. 7(a)), well matching with the characteristic cell adhesion and proliferation behaviours under the RGD environment. On the contrary, when the cells were incubated in CB[6]/DAH-HA hydrogels without the treatment of c(RGDyK)-CB[6], the proliferation of cells was low within the hydrogel network (FIG. 7(b)). The results suggested that the c(RGDyK)-CB[6] treatment not only resulted in the capture of c(RGDyK) peptides but also reconstituted a stable 3D RGD environment for the efficient cellular adhesion and proliferation.

Example 8

In Vivo Fluorescence Imaging of FITC-CB[6]@CB[6]/DAH Hydrogels

Encouraged by the in vitro results, we further investigated whether the CB[6]/DAH-HA hydrogels could be exploited for in vivo applications.

CB[6]-HA (100 μL, 3 wt %) and DAH-HA (100 μL, 3 wt %) were sequentially injected into the subcutis of the right and left side back of Balb/c nude mice (six-week old female, n=3). After gentle touching the back of the mice for 30 s to produce CB[6]/DAH-HA hydrogels, FITC-CB[6] (20 μL, 3 nM) and CF (20 μL, 3 nM) solutions were injected into the hydrogel on the right and left back of the mice, respectively. At 0, 1, 4, 7 and 11 days post-injection, in vivo images of the fluorescence from the mice were obtained on a Xenogen IVIS system (Caliper Life Science).

Figure 8:
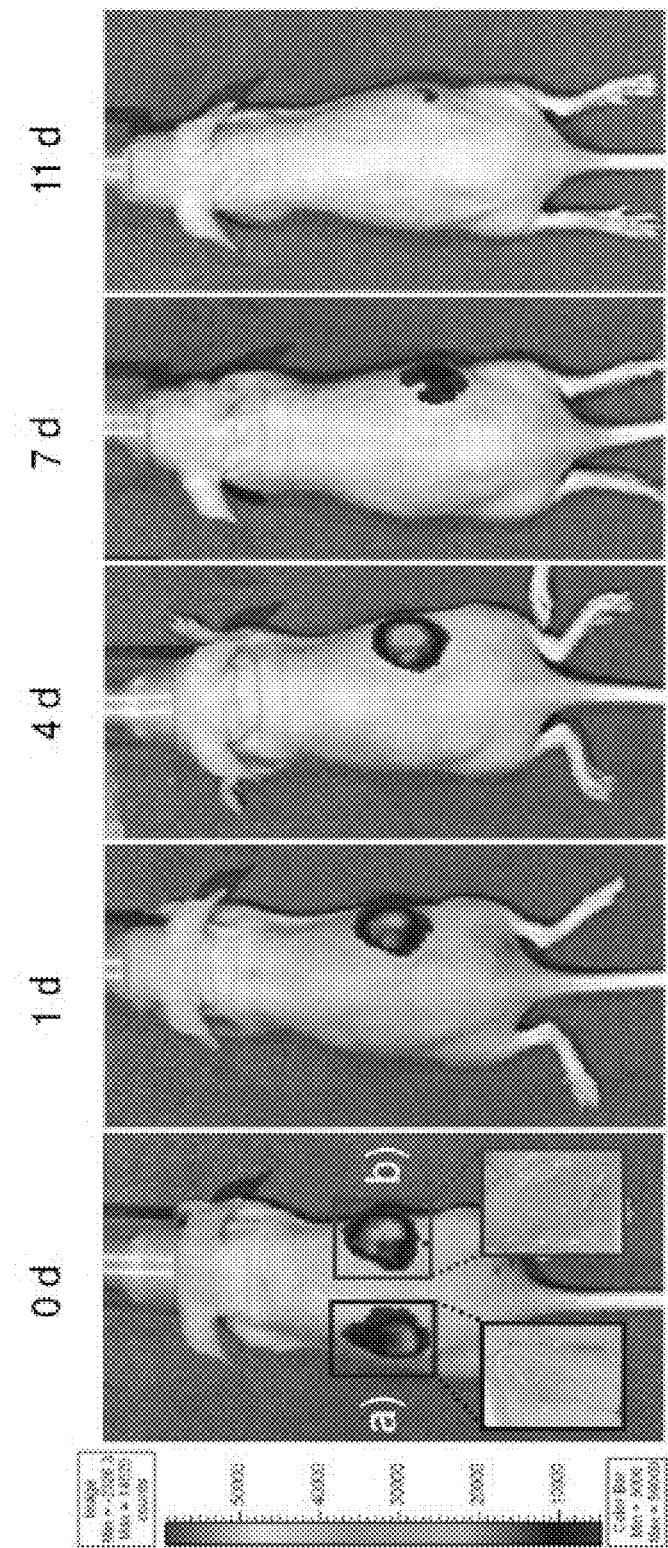
FIG. 8 shows in situ formation of CB[6]/DAH-HA hydrogel by sequential injections of CB[6]-HA solution (100 μL, 3 wt %) and DAH-HA solution (100 μL, 3 wt %), and modular modification by the injection of (a) CF solution (20 μL, 3 μM) for CF@CB[6]/DAH-HA hydrogel as a control and (b) FITC-CB[6] solution (20 μL, 3 μM) for FITC-CB[6]@CB[6]/DAH-HA hydrogel under the skin of the left and right back of nude mice (n=3), wherein in vivo fluorescence images of live mice were taken with increasing time for 11 days to assess the modular modification and the complex stability on the back of mice.

As shown in FIG. 8, in situ formation of the hydrogel under the skin of nude mice was confirmed after sequential subcutaneous injections of CB[6]-HA and DAH-HA solutions. The hydrogel was formed within a few min post-injection and stably kept its shape for longer than 2 weeks. In addition, we could demonstrate in situ modular modification of the hydrogel by simple injection of FITC-CB[6] into the hydrogel. The in situ modified hydrogel with FITC-CB[6] on the right back of the mouse emitted fluorescence for the next 11 days whereas the hydrogel modified with carboxy-fluorescein (CF) on the left back of the mouse as a control lost its fluorescence within a day probably due to the lack of strong interactions between the dye molecule and the hydrogel (FIG. 8). The CB[6]/DAH-HA hydrogels remained stable for longer than 2 weeks. The in situ facile formation and modular modification of the hydrogels on the back of mice reflected the feasibility of CB[6]/PA-HA hydrogels as a 3D biomimetic artificial ECM for in vitro studies on cellular behaviours, cell therapy, and various tissue engineering applications.

Example 9

Histological Analysis of CB[6]/DAH-HA Hydrogel

Figure 13:
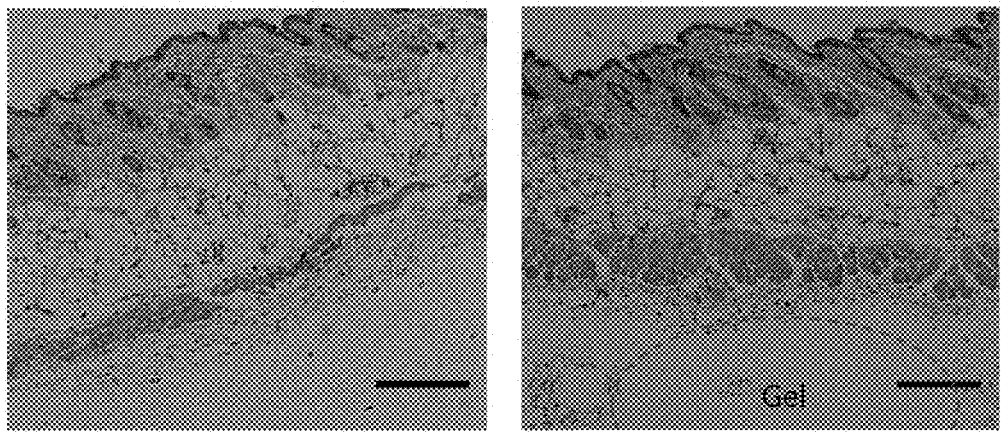
FIG. 13 shows the result of histological analysis of Balb/c mouse skin after staining with hematoxylin and eosin (H&E). (a) Normal mice without treatment as a control and (b) mice after treatment with CB[6]/DAH-HA hydrogel for a week (scale bar=200 μm).

The biocompatibility of CB[6]/DAH-HA hydrogels was assessed in Balb/c mice by the histological analysis after staining with hematoxylin and eosin (H&E) (FIG. 13). The CB[6]-HA solution (100 μL, 5 wt %) and the DAH-HA solution (100 μL, 5 wt %) were sequentially injected into the subcutis of the right side back of Balb/c mice (six-week old female, n=3). After 1 week post-injection, the implantation sites were completely excised and processed for the histological analysis. The biopsy samples were fixed in 4 vol. % formaldehyde solution, embedded in paraffin, sectioned at a thickness of 3 nm, and stained with H&E. The stained sample was observed with optical microscope.

The obtained results are shown in FIG. 13, indicating that the CB[6]/DAH-HA hydrogels resulted in a negligible inflammation with comparable numbers of macrophages (see FIG. 13(b)), and lymphocytes to those of normal mice (see FIG. 13(a)).

The inventors successfully developed biomimetic hydrogels for tissue engineering applications taking advantages of the strong and selective host-guest interaction between CB[6] in CB[6]-HA and PA in PA-HA. The supramolecular assembly of CB[6]-HA and PA-HA in the presence of cells resulted in the in situ formation of cell entrapped CB[6]/PA-HA hydrogels. Then, noncovalent, multifunctional, modular modification of 3D environments of the hydrogels could be performed by the simple treatment with various tags-CB[6]. Furthermore, in situ formation of the CB[6]/PA-HA hydrogel was also demonstrated under the skin of nude mice by sequential subcutaneous injections of CB[6]-HA and DAH-HA solutions. The modularly modified hydrogel with FITC-CB[6] on the right back of nude mice exhibited the fluorescence for up to 11 days, which suggested the feasibility of CB[6]/PA-HA hydrogels as a 3D biomimetic artificial ECM for various biomedical applications like in vitro studies on cellular behaviours, cell therapy, and tissue engineering.

What is claimed is:

1. A self-assembled conjugate comprising a compound of chemical formula I and a compound of chemical formula II:

[B]$m$-[H]$n$,    (chemical formula I)

[B]$m$-[G]$l$;    (chemical formula II)

in chemical formula I and II,

H is a cucurbit[n]uril n=5-12 having a functional group selected from the group consisting of an amine group, a carboxyl group, a hydroxyl group, an aldehyde group, an allyloxy group, a vinyl group, an acryl group, a thiol group, and a combination thereof;

G is selected from the group consisting of a C1-C20 aminoalkyl group having at least one amine group and a C1-C20 aminoalkyl group having metallocene;

B is a monomer of a polymer having a functional group selected from the group consisting of an amine group, a carboxyl group, a hydroxyl group, an aldehyde group, an allyloxy group, a vinyl group, an acryl group, a thiol group, and a combination thereof, wherein the polymer is at least one selected from the group consisting of polyethylene glycol (PEG), poly lactic acid (PLA), poly glycolic acid (PGA), poly lactic-co-glycolic acid (PLGA), hyaluronic acid, chitosan, dextran, and cellulose;

m, which is the number of the monomer, is an integer from 1 to 10,000; and n and l, which are the mole number of the host molecule or the guest molecule, respectively, are independently selected from integers from 1 to 10,000, wherein the ratio of m:n or 1 is 1:0.2 to 1:1, and the ratio of n:1 is 1:0.1 to 1:10, and wherein the equivalent ratio between the compound of chemical formula I and a compound of chemical formula II is 1:0.1 to 1:10 (equivalent of the compound of chemical formula I:equivalent of the compound of chemical formula II).

2. The self-assembled conjugate according to claim 1, wherein H is a cucurbit[n]uril n=6 or 7 linked with a functional group selected from the group consisting of an amine group, a hydroxyl group, an allyloxy group, and a combination thereof.

3. The self-assembled conjugate according to claim 1, wherein G is selected from the group consisting of spermine (SPM), diaminohexane (DAH), ferrocene methylamine, and a combination thereof.

4. The self-assembled conjugate according to claim 1, wherein B is a hyaluronic acid liked with a functional group selected from the group consisting of an amine group, a carboxyl group, a hydroxyl group, an aldehyde group, an allyloxy group, a vinyl group, an acryl group, a thiol group, and a combination thereof.

5. The self-assembled conjugate according to claim 1, which is in an aqueous solution form wherein the concentration of the self-assembled conjugate is 2 to 10%(w/v) to form a hydrogel.

6. A method for preparing a delivery composition of a bioactive material, comprising the step of:
providing a the self-assembled conjugate according to claim 1 and a bioactive material.

7. The method according to claim 6, wherein the bioactive material is at least one selected from the group consisting of a drug, a fluorescent material, a radioisotope, a target-oriented material, an imaging material, a cell, a protein drug, an antibody, and an aptamer.

8. The method according to claim 7, wherein the drug is at least one selected from the group consisting of paclitaxel, doxorubicin, docetaxel, 5-fluoreuracil, oxaliplatin, cisplatin, carboplatin, berberine, epirubicin, doxycycline, gemcitabine, rapamycin, tamoxifen, herceptin, avastin, tysabri, erbitux, campath, zevalin, humira, mylotarg, xolair, bexxar, raptiva, remicade, siRNA, aptamer, interferon, insulin, reopro, rituxan, zenapax, simulect, orthoclone, synagis, erythropoietin, epidermal growth factor (EGF), human growth hormone (hGH), thioredoxin, Fel d1, Bee Venom Phospholipase A2 (Api m1), myelin basic protein, Hsp60, and Chaperone DnaJ (Hsp 40).

9. The method according to claim 7, wherein the fluorescent material is at least one selected from the group consisting of fluorescein, rodamine, Dansyl, Cyanine dye (Cy), and antracene.

10. The method according to claim 7, wherein the radioisotope is at least one selected from the group consisting of $^3$H, $^{14}$C, $^{22}$Na, $^{35}$S, $^{33}$P, $^{32}$P, and $^{125}$I.

11. The method according to claim 7, wherein the target-oriented material is a peptide comprising at least one selected from the group consisting of RGD (arginine-leucine-aspartic acid), TAT (threonine-alanine-threonine), and MVm (methionine-valine-D-methionine); a peptide recognizing a specific cell; an antigen; an antibody; folic acid; nucleic acid; an aptamer; and a carbohydrate.

12. The method according to claim 7, wherein the imaging material is at least one selected from the group consisting of a gadolinium (Ga)-complex selected from gadolinium-diethylenetriamine penta-acetic acid (Ga-DTPA), gadolinium-diethylenetriamine penta-acetic acid-BMA (Ga-DTPA-BMA), gadolinium-tetraazacyclododecanetetraacetic acid (Ga-DOT), and Gadolinium-(1,4,8,11-tetraazacyclotetradecane) (Ga-cyclam); a nanoparticle of a metal selected from gold, silver, manganese, cadmium, selenium, tellurium, zinc, which has an average diameter of 1 to 200 nm; and a carbon nano-material selected from a single-walled carbon nanotube, a multi-walled carbon nanotube, fullerene, and graphene.

13. The method according to claim 7, wherein the cell is at least one selected from the group consisting of cancer cells, bone cells, skin cells, stomach cells, intestinal cells, lung cells, liver cells, brain cells, blood endothelial cells, immune cells, eythrocytes, leukocytes, lymphocytes, preosteoblasts, osteoblast, mesenchymal stem cell, and induced pluripotent stem cell.

14. A composition for tissue engineering containing the self-assembled conjugate according to claim 1 and one or more selected from the group consisting of a cell, a cell-differentiation inducer, a cell-proliferation accelerator, a cell-growth factor, and a cell-adsorption inducer.

15. The composition for tissue engineering according to claim 14, wherein the cell is at least one selected from the group consisting of cancer cells, bone cells, skin cells, stomach cells, intestinal cells, lung cells, liver cells, brain cells, blood endothelial cells, immune cells, eythrocytes, leukocytes, lymphocytes, preosteoblasts, osteoblast, mesenchymal stem cell, and induced pluripotent stem cell.

* * * * *